United States Patent [19]

Dickstein

[11] 4,285,076

[45] Aug. 25, 1981

[54] FLUSHING APPARATUS FOR ILEOSTOMY BAG

[76] Inventor: Samuel R. Dickstein, 705 S. Elk St., Hemet, Calif. 92343

[21] Appl. No.: 820,427

[22] Filed: Aug. 1, 1977

[51] Int. Cl.³ .......................................... E03D 11/00
[52] U.S. Cl. ...................................... 4/341; 4/300.2; 4/661
[58] Field of Search ............... 4/1, 341, 300.2, 661; 134/94, 102, 166 R, 167 R, 171, 172, 198; 128/227, 229, 240, 241, 248, 283

[56] References Cited

U.S. PATENT DOCUMENTS

| | | | |
|---|---|---|---|
| 2,023,007 | 12/1935 | Delano | 134/166 R |
| 2,568,857 | 9/1951 | Jacobs | 4/1 |
| 2,811,975 | 11/1957 | Tatibana | 134/102 |
| 2,834,026 | 5/1958 | Kronish | 4/1 |
| 2,894,263 | 7/1959 | Kunkel et al. | 4/1 |
| 3,677,242 | 7/1972 | Shaye | 128/227 |

*Primary Examiner*—Willis Little
*Attorney, Agent, or Firm*—Keith D. Beecher

[57] ABSTRACT

Flushing apparatus is provided for cleaning and flushing out ileostomy bags. The apparatus includes a bracket which is adapted to fit over a toilet and which includes an upright open-ended tubular support member. A second tubular member with a funnel top is adapted to fit into the tubular support member of the bracket in telescoping relationship. The second tubular member is coupled to a source of flush water, and a flexible tube is provided which extends upwardly through the funnel member to receive the mouth of the ileostomy bag when the bag (worn by the patient) is positioned over the top of the funnel member, and which introduces flush water into the interior of the bag, and which serves to flush the contents of the bags down through the second tubular member and into the toilet, below the water level in the toilet to prevent splashing.

6 Claims, 3 Drawing Figures

FLUSHING APPARATUS FOR ILEOSTOMY BAG

BACKGROUND OF THE INVENTION

As noted briefly above, the present invention is concerned with improved apparatus for flushing out the bags worn by persons who have undergone an ileostomy operation. The principal objective of the invention is to provide apparatus which is convenient to use, and which provides a simple flushing means, whereby the ileostomy bag may be thoroughly flushed out and cleaned in a relatively short time, and with a minimum of inconvenience on behalf of the wearer.

DETAILED DESCRIPTION OF THE ILLUSTRATED EMBODIMENT

Figure 1:
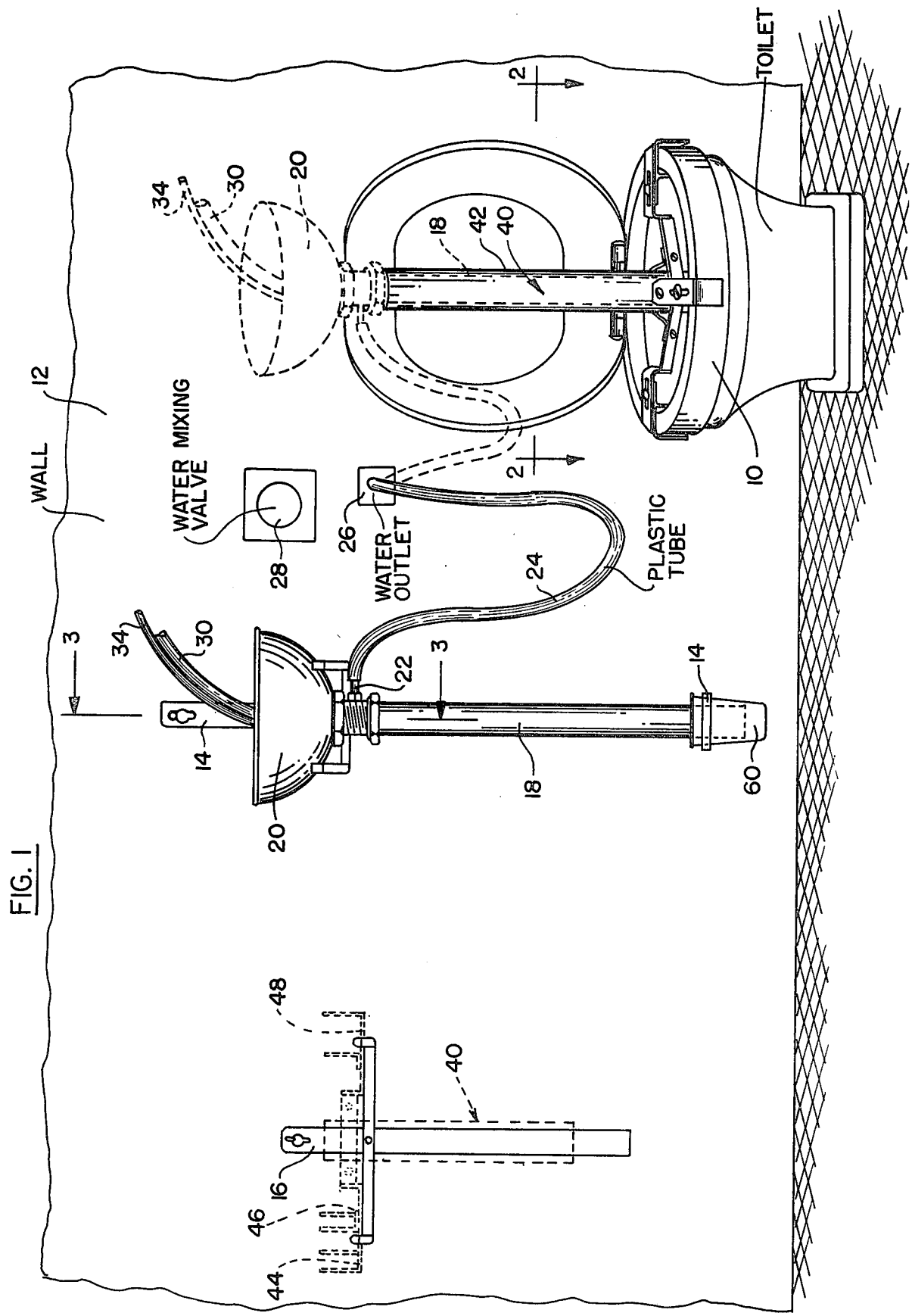
FIG. 1 is a schematic representation showing the apparatus of the invention installed in a typical bathroom for use by an ileostomy bag wearer.

FIG. 1 shows a typical toilet 10 which is positioned in a bathroom adjacent a wall 12. A bracket 14 may be mounted on the wall 12 for supporting one of the components of the apparatus of the invention, and a second bracket 10 may be mounted on the wall for supporting a second embodiment of the apparatus of the invention. A cup 60 may be supported on the lower end of bracket 14 to receive drippings.

Figure 3:
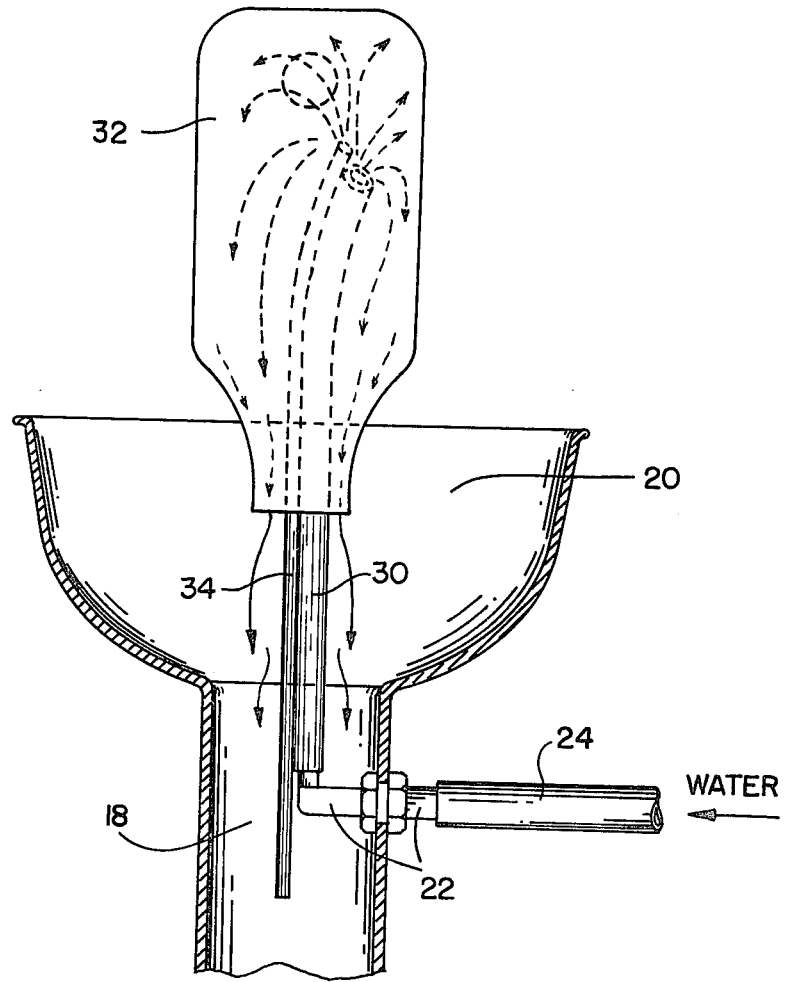
FIG. 3 is a section taken essentially along the line 3—3 of FIG. 1.

The first component of the apparatus of the invention includes a tubular member 18 having a cup-shaped funnel member 20 mounted at its upper end. A fitting 22 is mounted in the upper end of tubular member 18, as best shown in FIG. 3. An elongated flexible tube 24 formed of plastic, or other appropriate material is coupled to one end of the fitting 22. Tube 24 is coupled to a water outlet 26. Pressurized water from outlet 26 is controlled by the patient, as to pressure and temperature, by a typical water mixing valve 28 mounted on the wall 12 adjacent to the toilet 10.

A second flexible tube 30 is coupled to the other end of fitting 22, and tube 30 extends upwardly in funnel 20 to receive the mouth of an ileostomy bag 32, as worn by the patient, and to extend into the interior of the bag. A further tube 34 is mounted against the side of tube 30, and likewise extends into the interior of bag 32 to act as an air relief for the interior of the bag.

Figure 2:
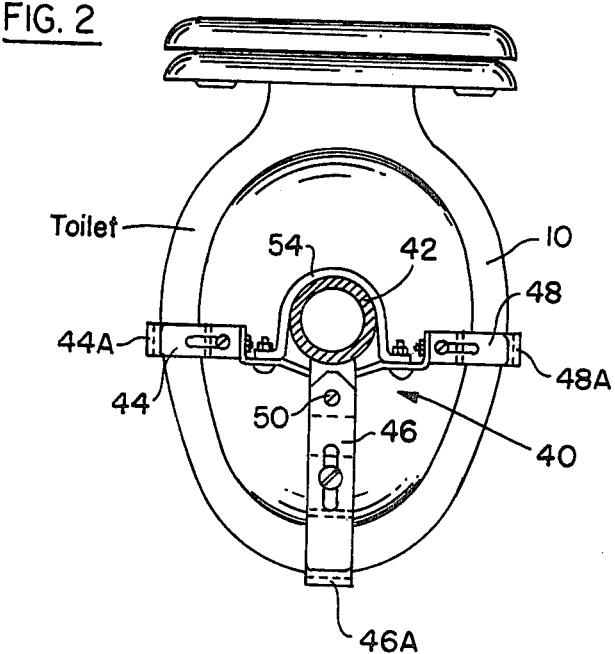
FIG. 2 is a section taken along the line 2—2 of FIG. 1.

The first component of the invention, which includes the tubular member 18 and funnel 20, is supported over toilet 10 by a bracket 40. The bracket 40 includes an upright open-ended tubular member 42 which is supported over the toilet 10 by three radial arms designated 44, 46 and 48 in FIG. 2. The arms 44, 46 and 48 have adjustable brackets 46A, 48A and 44A at their respective ends, so as to adapt the bracket 40 to different sized toilets. Also, the arm 46 is pivoted by means of a screw 50, so that it may be folded into the plane of arms 44 and 48 to facilitate the support of the bracket 40 on wall bracket 16, when the apparatus is not in use.

To use the apparatus, bracket 40 is first placed over the open toilet 10 in the position shown in FIG. 1, and the tubular member 18 is inserted into the tubular member 42 so that the tubular member 18 and its funnel 20 may be supported, in the manner shown by the broken lines in FIG. 1, within the tubular member 42 of the support bracket 40. It should be noted that the arms 44, 46 and 48 are supported on the upright tubular member 42 by means of a strap 54, and the strap is adjustable along the tubular member 40 so as to accommodate the apparatus to the particular height of the person using the apparatus.

To flush out the ileostomy bag, the person wearing the bag stands over the funnel 20 supported in the upright tubular member 42 of bracket 40, and he opens the mouth of the ileostomy bag, but holds the bag closed with his hand. He then inserts the upper ends of tubes 30 and 34 into the mouth of the ileostomy bag 32, as shown in FIG. 3, and turns on the mixing valve 28 so that pressurized water of the desired temperature and pressure flows into the interior of bag 32 to flush the contents of the bag out through the mouth of the bag and into the tubular member 18 through the funnel 20. The contents are then flushed down through tubular member 18 and into the toilet. Tubular member 18 extends below the water level in the toilet, to prevent splashing.

If desired, fitting 22 may be a T-type fitting, so as to permit the user to inject liquid soap, detergent or deodorant into the pressurized stream of water entering the bag 32. It is also with the contemplation of the invention that funnel 20 and tubular member 18 be permanently attached to the bathroom wall at a convenient height for use; and the lower end of tubular member 18 be coupled through a usual U-shaped waste trap to the discharge pipe extending from the bathroom to the sewer system. Such an assembly obviates any need for the toilet or for the separate holding racks.

It is obvious that the assembly of the invention can also be used as a urinal, with funnel 20 being appropriately shaped for female patients.

The invention provides, therefore, apparatus for use by persons who have undergone ileostomy operations, and which is simple and convenient to use, and by which the ileostomy bags may be thoroughly and expeditiously flushed.

While a particular embodiment of the invention has been shown and described, modifications may be made. It is intended in the claims to cover all embodiments which come within the true spirit and scope of the invention.

What is claimed is:

1. Apparatus for flushing the contents of an ileostomy bag into a toilet, said apparatus including in combination: an elongated tubular member; an open-topped funnel member attached to the upper end of said tubular member; first conduit means extending into the funnel member and upwardly through the open top thereof to be inserted into the mouth of an ileostomy bag held over the top of said funnel member; a second conduit means for introducing pressurized liquid from a pressurized liquid source through said first conduit means and into the interior of the ileostomy bag held over said funnel member to flush the contents of the ileostomy bag into the funnel member and through the tubular member; and bracket means for supporting the elongated tubular member and the attached funnel member over a toilet.

2. The apparatus defined in claim 1, in which the first and second conduit means each comprises an elongated flexible tube.

3. The apparatus defined in claim 2, and which includes a third elongated flexible tube extending with the elongated tube comprising said first conduit means into the mouth of the ileostomy bag to constitute an air relief conduit for the interior of the ileostomy bag.

4. The apparatus defined in claim 1, in which said bracket means includes an upright open-ended tubular member for removably receiving the first-named tubular member in telescopic relationship therewith, and a plurality of radially extending support arms attached to the lower end of said open-ended tubular member and positioned to extend over the rim of the supporting toilet to be removably supported thereto.

5. The apparatus defined in claim 4, in which the support arms are adjustable to fit different sized toilets.

6. The combination defined in claim 4, in which said support arms are foldable into a common plane.

* * * * *